US00PP11581P

United States Patent [19]

Dümmen

[11] Patent Number: Plant 11,581

[45] Date of Patent: Oct. 17, 2000

[54] NEW GUINEA IMPATIENS PLANT NAMED 'DUERIWHITEYE'

[75] Inventor: Marga Dümmen, Rheinberg, Germany

[73] Assignee: Dümmen Jungpflanzenkulturen, Rheinberg-Eversael, Germany

[21] Appl. No.: 09/225,827

[22] Filed: Jan. 5, 1999

[51] Int. Cl.[7] ..... A01H 5/00

[52] U.S. Cl. ..... Plt./318

[58] Field of Search ..... Plt./318

*Primary Examiner*—Howard J. Locker
*Assistant Examiner*—Michelle Kizilkaya
*Attorney, Agent, or Firm*—C. A. Whealy

[57] ABSTRACT

A new and distinct cultivar of New Guinea Impatiens plant named 'Dueriwhiteye', characterized by its rounded flowers that are white with a pink "eye" zone; freely flowering; freely branching plant habit; dark green leaves that contrast well with the white flower color.

1 Drawing Sheet

BACKGROUND OF THE INVENTION

The present invention relates to a new and distinct cultivar of New Guinea Impatiens plant, botanically known as *Impatiens hawkeri*, and hereinafter referred to by the name 'Dueriwhiteye'. The new cultivar is marketed under the name Riviera White Eye.

The new cultivar is a product of a planned breeding program conducted by the Inventor in Rheinberg, Germany. The objective of the breeding program is to develop New Guinea Impatiens that are freely branching; early flowering; and that have desirable flower and leaf colors.

The new cultivar originated from a cross made by the Inventor of the *Impatiens hawkeri* proprietary selection identified as D6 as the female, or seed, parent with the *Impatiens hawkeri* proprietary selection identified as K2 as the male, or pollen, parent.

'Dueriwhiteye' was discovered and selected by the Inventor as a single flowering plant within the progeny of the stated cross in a controlled environment in Rheinberg, Germany.

Asexual reproduction of the new cultivar by terminal cuttings taken at Rheinberg, Germany, has shown that the unique features of this new cultivar are stable and reproduced true to type in successive generations of asexual reproduction.

BRIEF SUMMARY OF THE INVENTION

The following traits have been repeatedly observed and are determined to be the unique characteristics of 'Dueriwhiteye'. These characteristics in combination distinguish 'Dueriwhiteye' as a new and distinct cultivar:

1. Rounded flowers that are white with a pink "eye" zone.
2. Freely flowering.
3. Freely branching plant habit.
4. Dark green leaves that contrast well with the white flower color.

Compared to plants of the female parent, plants of the new cultivar have larger and more rounded flowers. Compared to plants of the male parent, plants of the new cultivar are more vigorous and have larger flowers with a larger "eye" zone.

The new cultivar can be compared to the commercial 'Samoa' (disclosed in U.S. Plant Pat. No. 8,422). However, plants of the new cultivar have stronger, more durable flowers with a larger pink "eye" zone than plants of the cultivar Samoa.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plant of 'Dueriwhiteye' grown in a 12-cm container.

DETAILED BOTANICAL DESCRIPTION

Plants of 'Dueriwhiteye' have not been observed under all possible environmental conditions. The phenotype may vary somewhat with variations in environment such as temperature, daylength and light intensity, without, however, any variance in genotype. The following observations and measurments describe plants grown in 12-cm containers during the fall in Rheinberg, Germany, under commercial practice in a glass-covered greenhouse with day and night temperatures about 18° C. and light levels about 45 klux.

In the following description, color references are made to The Royal Horticultural Society Colour Chart except where general terms of ordinary dictionary significance are used.

Botanical classification: *Impatiens hawkeri* 'Dueriwhiteye'.

Parentage:

- *Female, or seed, parent*.—Proprietary seedling selection of *Impatiens hawkeri* identified as D6.
- *Male, or pollen, parent*.—Proprietary seedling selection of *Impatiens hawkeri* identified as K2.

Propagation:

- *Type cutting*.—Terminal cuttings.
- *Time to initiate roots*.—Summer: About 10 days at 22° C. Winter: About 12 days at 22° C.
- *Time to develop roots*.—Summer: About 21 days at 22° C. Winter: About 24 days at 22° C.
- *Rooting habit*.—Freely branching.

Plant description:

- *General appearance*.—Rounded; dense; very freely and basally branching; upright and spreading; moderate growth rate and vigor; most suitable for 12 to 13-cm pots. About 15 to 16 weeks are required to produce a finished 12-cm container from an unrooted cutting.
- *Plant height*.—About 17 cm from soil level to top of plant plane.

*Lateral branches*.—Length: About 9 cm. Diameter: About 3.9 mm. Internode length: About 2.8 cm. Color: 136A.

*Foliage description*. —Quantity of leaves per lateral branch: About 18. Shape: Elliptic with apiculate apex and attenuate base. Length: About 8.7 cm. Width: About 4.3 m. Texture: Smooth, leathery and glabrous. Margin: Serrulate. Color: Young foliage, upper surface: 139A. Young foliage, lower surface: 139B. Mature foliage, upper surface: 136A. Mature foliage, lower surface: 132C. Veins, upper surface: 146B. Veins, lower surface: 139A. Petiole: Length: About 1.7 cm. Diamter: About 2.5 mm. Color: 53B.

Flower description:

*Flowering habit*.—Freely flowering.

*Natural flowering season*.—Year-round. Plants flower about 8 weeks after planting. Flowering intermittent.

*Rate of flower opening*.—About 2 to 3 days.

*Flower longevity*.—About 10 to 12 days.

*Flowers borne*.—Flower buds develop in apical leaf axils. Open flowers are displayed above the foliage.

*Quantity of inflorescences*.—Extremely floriferous; usually about 85 buds and flowers per plant.

*Flower shape*.—Rounded.

*Flower diameter*.—About 6 cm.

*Petals*.—Shape: Reniform/cordate with emarginate apex and acute base. Quantity, arrangement: 5 petals overlapping. Aspect: Flat and slightly rippled. Length: About 3 cm. Width: About 4.2 cm. Texture: Smooth, satiny, and glabrous. Margin: Entire. Color: When opening, upper surface: White 155D, background with faint pink, 55C, "eye" zone. When opening, lower surface: White, 155D. Fully opened, upper surface: White, 155D, background with pink 64D–66D, "eye" zone. Fully opened, lower surface: White, 155D.

*Peduncle*.—Angle: Erect. Length: About 3.8 cm. Color: 137B.

*Flower bud*.—Shape: Ovoid with spur. Length: About 1.6 cm. Diameter: About 1.1 cm. Color: 54D.

*Spur*.—Shape: Needle-shaped, curved at end. Length: About 4.8 cm. Color: 53A.

*Reproductive organs*.—Androecium: Stamen number: 5. Anther shape: Oval. Anther size: About 5 mm. Anther color: 49B. Pollen color: 158B. Amount of pollen: Abundant. Gynoecium: Pistil length: About 5 mm. Stigma color: 143A. Ovary color: 143C.

Disease resistance: Resistance to known pathogens of New Guinea Impatiens has not been observed.

Seed development: Seed production has not been observed.

It is claimed:

1. A new and distinct cultivar of New Guinea Impatiens plant named 'Dueriwhiteye', as illustrated and described.

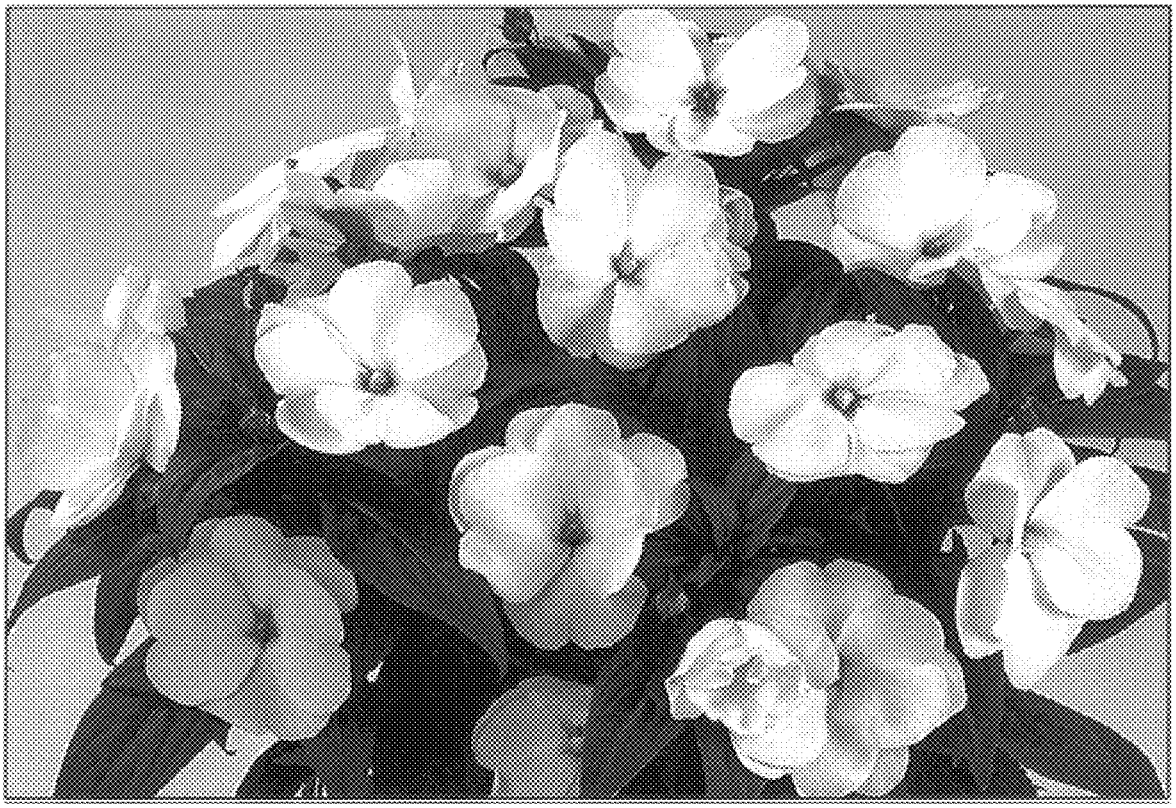

* * * * *